United States Patent
Chua et al.

(10) Patent No.: US 7,098,462 B2
(45) Date of Patent: Aug. 29, 2006

(54) MICROFABRICATED DEVICE FOR SELECTIVELY REMOVING AND ANALYZING AIRBORNE PARTICULATES FROM AN AIR STREAM

(75) Inventors: Beelee Chua, Davis, CA (US);
Anthony S. Wexler, Davis, CA (US);
Norman C. Tien, Davis, CA (US);
Debbie A. Niemeier, Davis, CA (US);
Britt A. Holmén, Storrs, CT (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 11/036,648

(22) Filed: Jan. 14, 2005

(65) Prior Publication Data

US 2005/0156118 A1 Jul. 21, 2005

Related U.S. Application Data

(60) Provisional application No. 60/536,935, filed on Jan. 16, 2004.

(51) Int. Cl.
*H01J 27/00* (2006.01)

(52) U.S. Cl. .............................. 250/426; 95/78; 95/96; 95/97; 204/164; 422/186.07

(58) Field of Classification Search ................ None
See application file for complete search history.

(56) References Cited

U.S. PATENT DOCUMENTS 6,495,823 B1* 12/2002 Miller et al. ................ 250/286
6,783,575 B1*  8/2004 Pasic et al. ..................... 96/44
2005/0051028 A1*  3/2005 Botvinnik ....................... 96/88

* cited by examiner

*Primary Examiner*—John R. Lee
*Assistant Examiner*—Zia R. Hashmi
(74) *Attorney, Agent, or Firm*—Park, Vaughan & Fleming LLP; Edward J. Grundler (57) ABSTRACT

One embodiment of the present invention provides a system for ionizing airborne particulates. The system includes an insulating substrate and a first electroplated structure on the insulating substrate. This first electroplated structure includes an anchor and a probe structure on the anchor that is separate from the insulating substrate. A second electroplated structure is included on the insulating substrate. The first electroplated structure and the second electroplated structure form a unipolar corona discharge based ionizer

26 Claims, 6 Drawing Sheets

MICROFABRICATED DEVICE FOR SELECTIVELY REMOVING AND ANALYZING AIRBORNE PARTICULATES FROM AN AIR STREAM

RELATED APPLICATION

This application hereby claims priority under 35 U.S.C. §119 to U.S. Provisional Patent Application No. 60/536,935, filed on 16 Jan. 2004, entitled "A Microfabricated Ionizer structure Based on Unipolar Corona Discharge," by inventors Beelee Chua, Norman C. Tien, Anthony S. Wexler, and Debbie A. Niemeier, which is incorporated herein by reference.

BACKGROUND

1. Field of the Invention

The present invention relates to an airborne particulate analyzer. More specifically, the present invention relates to a microfabricated device for selectively removing and analyzing airborne particulates from an air stream.

2. Related Art

A number of techniques are presently used to separate airborne particulate matter from an air stream in order to determine the size and possibly type and quantity of particulates in the air stream, and to filter the air stream. These particulates can include environmental pollution and pathogens, such as bacteria and viruses.

Current approaches to separating airborne particulate matter involve using large devices, some of which require a radio-active ionization source. This is particularly true for devices used for separating particulates smaller than 100 nm in size. These devices typically grow particulates to an optimal size after separation to facilitate optical counting. Handheld devices do not exist that are capable of separating and counting particulates smaller than 100 nm. Detection of particulates smaller than 100 nm is advantageous because it includes airborne pathogens such as viruses.

The techniques used to detect particulates optically are limited to discrete size bins. These devices are only capable of detecting specific size particulates (i.e. 100 nm, 300 nm, 500 nm, etc). They cannot, however, be re-configured to give values for 150 nm, 180 nm, etc. This is because a specific wavelength that is equivalent to the particulate size is required for their detection. In order to count all particulates, a laser source or array of laser sources to give a continuous wavelength spectrum is required. This is prohibitively expensive.

Current portable devices are not able to determine the composition of the particulates, and hence provide little benefit in detecting chemical and/or biological agents. On the other hand, devices which are able to detect these chemical and biological agents are typically laboratory devices, which are unsuitable for field work.

The size of current particulate analyzers that are able to detect particulates smaller than 100 nm precludes using them in portable devices, and the substantial price of these particulate analyzers makes ubiquitous positioning within an urban area prohibitively expensive.

Hence, what is needed is a portable apparatus, which can effectively size and count particulates smaller than 100 nm in an air stream without the drawbacks cited above. Determining the actual size of the particulates is advantageous because it can possibly lead to determining the source of the particulates.

SUMMARY

One embodiment of the present invention provides a system for ionizing airborne particulates. The system includes an insulating substrate with a first electroplated structure which resides on the insulating substrate. This first electroplated structure includes an anchor with a probe structure that is separate from the insulating substrate. A second electroplated structure also resides on the insulating substrate. The first electroplated structure and the second electroplated structure are configured to collectively form a unipolar corona discharge based ionizer.

In a variation of this embodiment, the second electroplated structure forms a collection grid.

In a further variation, the second electroplated structure is comprised of parallel structures, wherein the probe structure is centered between the parallel structures, so that an electrical field formed between the probe structure and the parallel structures is perpendicular to the air flow through the apparatus.

In a further variation, the system additionally includes differential mobility separator plates, which are configured to allow selected particles to be passed to a Faraday's cup for counting.

In a further variation, the system includes differential mobility separator plates, which are configured to collect selected particles for counting.

In a further variation, the system includes segmented differential mobility separator plates, wherein each segment of the segmented differential mobility separator plates collects a different mobility particle for counting.

In a further variation, the system includes differential mobility separator plates, which are configured to separate particulate matter from an air flow, whereby the apparatus forms a filter mechanism.

In a further variation, the probe structure is isolated from the main air flow through the apparatus, thereby providing ozone to the main air flow.

In a further variation, the apparatus is configured so that the main air flow (including ozone) is bubbled through water, wherein the ozone kills nano-organisms such as bacteria and viruses in the water.

DETAILED DESCRIPTION

The following description is presented to enable any person skilled in the art to make and use the invention, and is provided in the context of a particular application and its requirements. Various modifications to the disclosed embodiments will be readily apparent to those skilled in the art, and the general principles defined herein may be applied to other embodiments and applications without departing from the spirit and scope of the present invention. Thus, the present invention is not intended to be limited to the embodiments shown, but is to be accorded the widest scope consistent with the principles and features disclosed herein.

Corona Ionizer

Figure 1A:
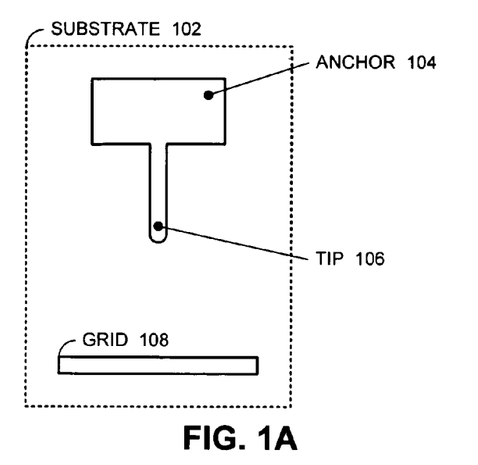
FIG. 1A presents a top view of a microfabricated corona ionizer in accordance with an embodiment of the present invention.

FIG. 1A presents a top view of a microfabricated corona ionizer in accordance with an embodiment of the present invention. The components of the microfabricated corona ionizer are deposited on an insulating substrate 102. One possible material for insulating substrate 102 is glass. Anchors 104 and 110 (see FIG. 1C) are deposited on substrate 102. A typical material for anchors 104 and 110 is copper.

Probe 106 is deposited with anchor 104 but is undercut so that it is suspended above substrate 102. The radius of the tip of probe 106 is less than approximately 20 µm, while the suspension height of probe 106 above substrate 102 is typically less than 500 µm. Collection grid 108 extends from anchor 110 and is typically spaced less than 3 mm from the tip of probe 106.

During operation, a voltage is applied between probe 106 and collection grid 108. This voltage is typically in the range of two kilovolts. In this configuration, the ionizer uses less than 150 milliwatts and has a footprint of approximately 1 centimeter square. The ionizer is able to charge more than 6 million nanoparticulates per second per device. Note that the inception voltage is dependent only upon the inter-electrode spacing and is independent of the radius of curvature of the tip of probe 106.

Figure 1B:
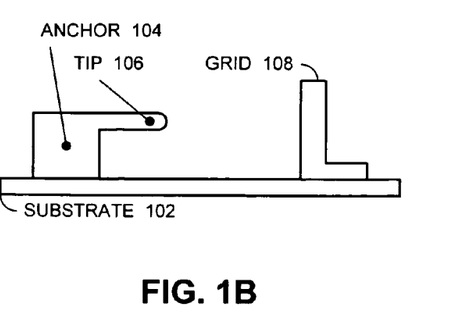
FIG. 1B presents a side view of a microfabricated corona ionizer in accordance with an embodiment of the present invention.

FIG. 1B presents a side view of a microfabricated corona ionizer in accordance with an embodiment of the present invention. The view presented in FIG. 1B clearly shows how probe 106 is suspended above substrate 102 and the relationship between probe 106 and collection grid 108.

Figure 1C:
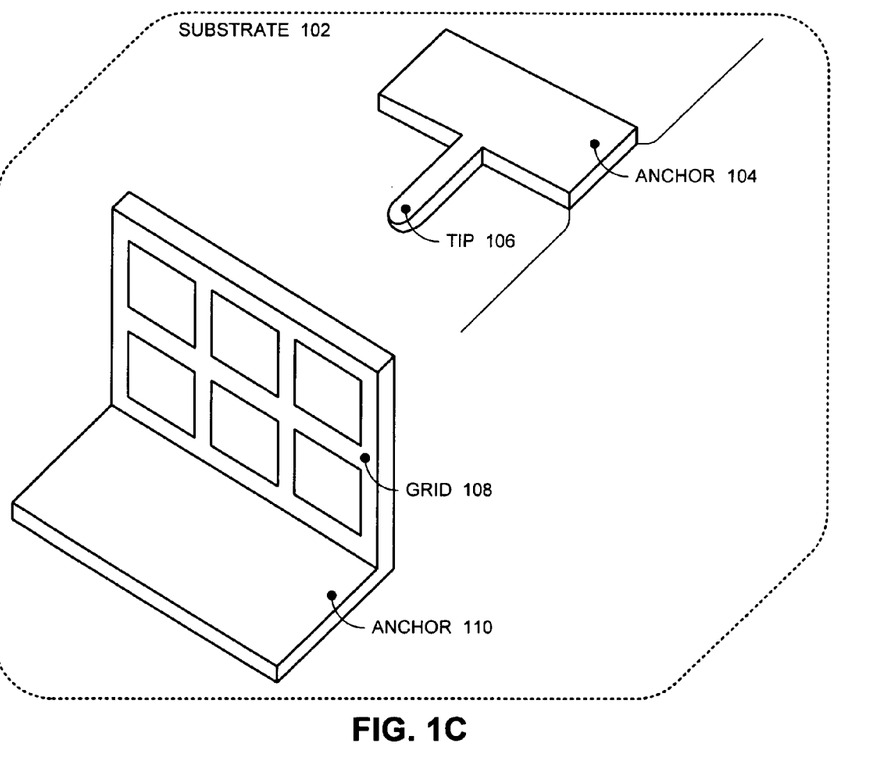
FIG. 1C presents an orthogonal view of a microfabricated corona ionizer in accordance with an embodiment of the present invention.

FIG. 1C presents an orthogonal view of a microfabricated corona ionizer in accordance with an embodiment of the present invention. This view is presented to further clarify the relationships among the components of the microfabricated corona ionizer.

Corona Ionizer with Parallel Plates

Figure 2:
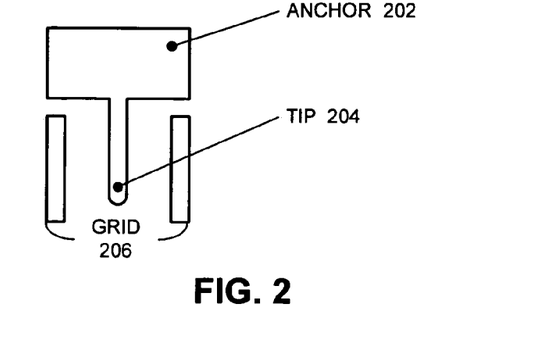
FIG. 2 illustrates a microfabricated corona ionizer with parallel plates in accordance with an embodiment of the present invention.

FIG. 2 presents a microfabricated corona ionizer with parallel plates in accordance with an embodiment of the present invention. Anchor 202 and probe 204 are deposited on a substrate (not shown) using techniques similar to those described above for anchor 104 and probe 106. Grids 206 and supporting anchors are deposited on the substrate such that they are parallel to probe 204 and equidistant from probe 204. In this configuration, the corona ionizer forms a flow-through ionizer, which is useful for creating microfabricated particulate sensors.

Basic Particulate Sensor

Figure 3:
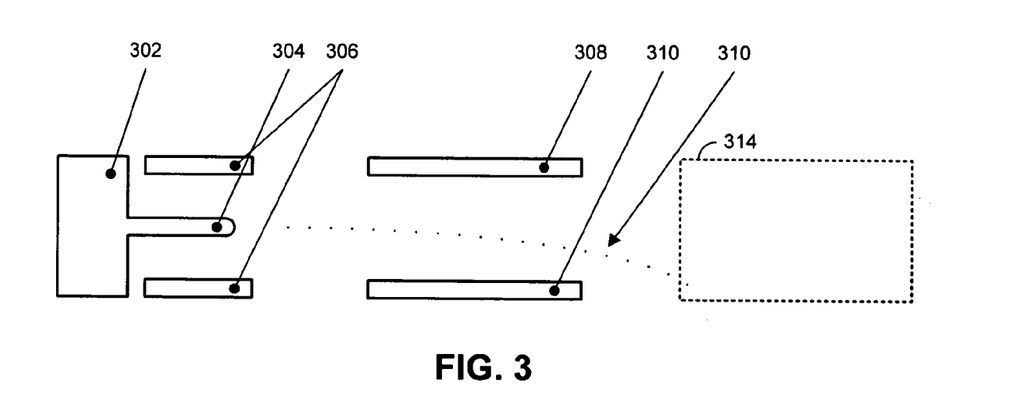
FIG. 3 illustrates a particulate sensor in accordance with an embodiment of the present invention.

FIG. 3 illustrates a particulate sensor in accordance with an embodiment of the present invention. Anchor 302, probe 304, and grids 306 form a corona ionizer as described above with reference to FIG. 2. Differential mobility separator plates 308 and 310 are deposited on the substrate such that airflow passing the ionizer is directed between mobility separator plates 308 and 310. When a potential difference is applied between mobility separator 308 and 310, an electric filed is created between them.

When charged particulates enter the space between mobility separator plates 308 and 310, they are deflected by the electric field. The amount of deflection is dependent upon the mobility of the particulates and the strength of the applied field. By varying the voltage applied to mobility separator plates 308 and 310, particulates of different mobility can be made to impinge on the Faraday's cup 314. The current generated by this impingement can be measured to determine the concentration of particulates with a given mobility. Note that particulates of different mobility can also be made to impinge on mobility separator plate 310 and the resultant current can be measured to determine the concentration of particulates with a given mobility.

Segmented Particulate Sensor

Figure 4:
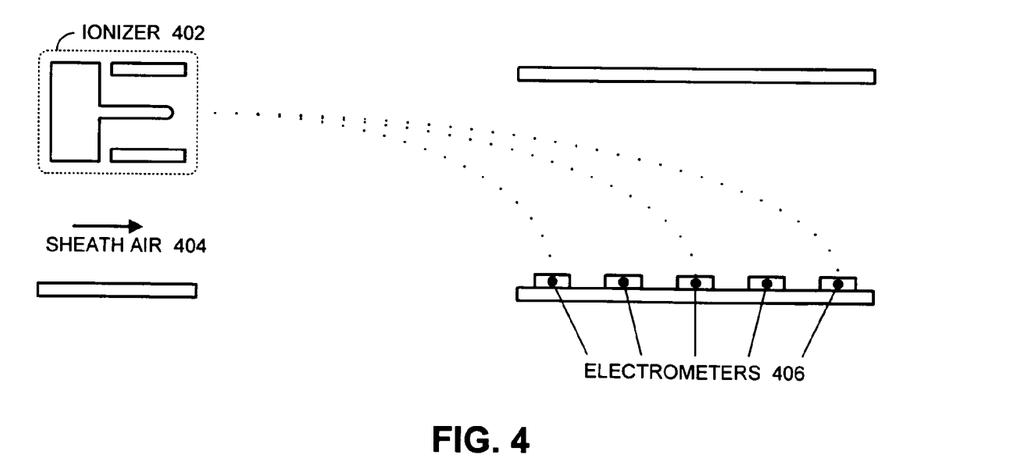
FIG. 4 illustrates a segmented particulate sensor in accordance with an embodiment of the present invention.

FIG. 4 illustrates a segmented particulate sensor in accordance with an embodiment of the present invention. Ionizer 402 is deposited on the substrate as described above in reference to FIG. 2. Each segment of segmented mobility separator plate 406 can be biased to a different voltage. In this configuration, particulates with multiple mobilities can be measured simultaneously. Sheath air 404 is a source of clean air. Note that sheath air 404 can be a clean gas other than air, such as clean nitrogen.

Filter Mechanism

Figure 5:
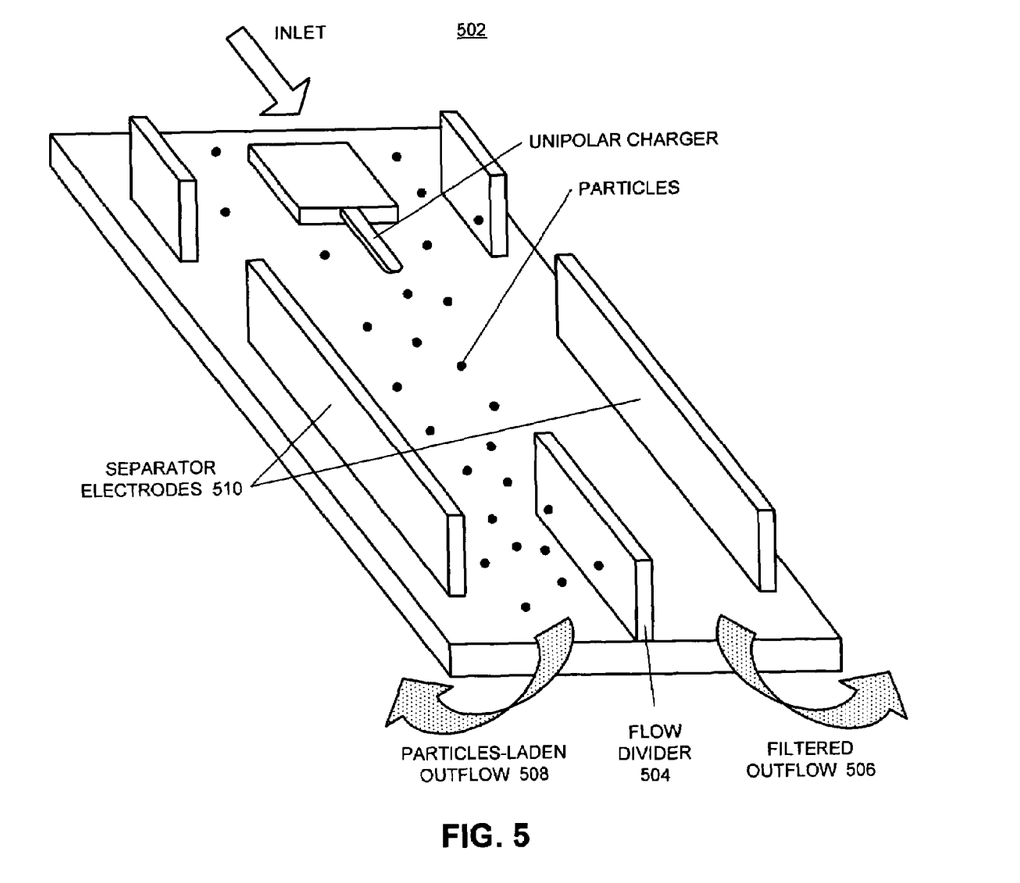
FIG. 5 illustrates a filter mechanism in accordance with an embodiment of the present invention.

FIG. 5 illustrates a filter mechanism 502 in accordance with an embodiment of the present invention. Filter mechanism 502 is constructed as described above in conjunction with FIG. 3 with the addition of flow divider 504. Flow divider 504 channels filtered air out of portal 506, while particulates are channeled out of portal 508. By applying a proper bias to separator electrodes 510, the ionized particulates are channeled to portal 508.

Combined Filter and Segmented Particulate Sensor

Figure 6:
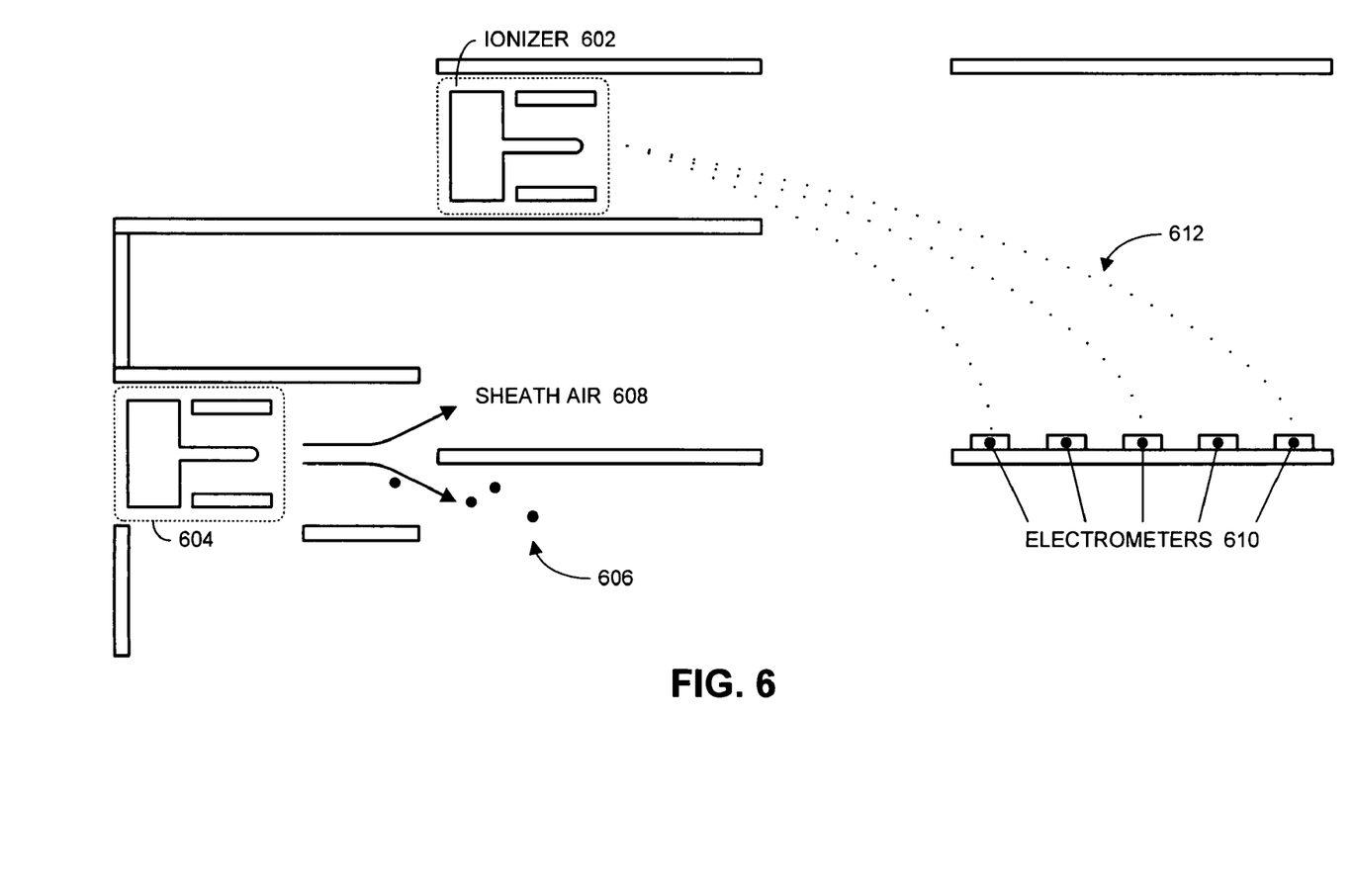
FIG. 6 illustrates using a filter mechanism in conjunction with a segmented particulate sensor in accordance with an embodiment of the present invention.

FIG. 6 illustrates using a filter mechanism in conjunction with a segmented particulate sensor in accordance with an embodiment of the present invention. Ionizer 604 filters its input air rejecting particulates 606, thus providing clean air 608 as the sheath air. Ionizer 602 ionizes particulates in the incoming sample. These ionized particulates 512 are selected for measurement by segmented mobility separator plate 610 as described above in conjunction with FIG. 4.

Ozone Generator

Figure 7:
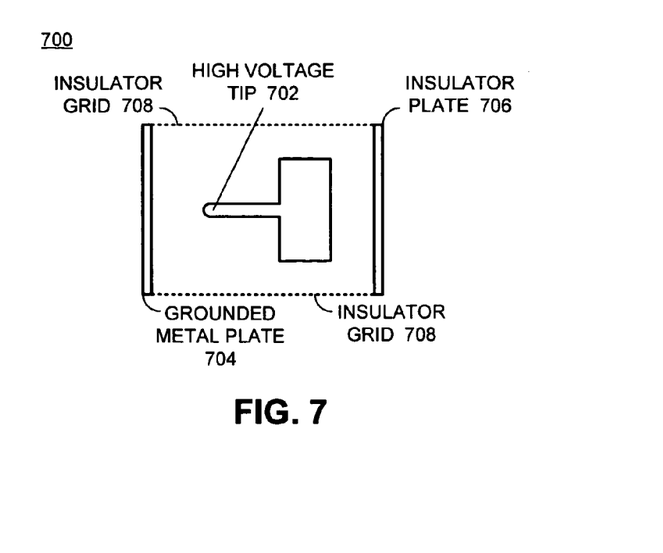
FIG. 7 illustrates an ozone generator in accordance with an embodiment of the present invention.

FIG. 7 illustrates an ozone generator 700 in accordance with an embodiment of the present invention. Ozone generator 700 includes a high voltage tip 702, a grounded metal plate 704, and insulator plate 706, and an insulator grid 708. High voltage tip 702 and grounded metal plate 704 form a microfabricated corona discharge ionizer which creates ozone during operation. The ozone diffuses through the insulator grid 708 into the surrounding air.

Ozone Diffusing Unit

Figure 8:
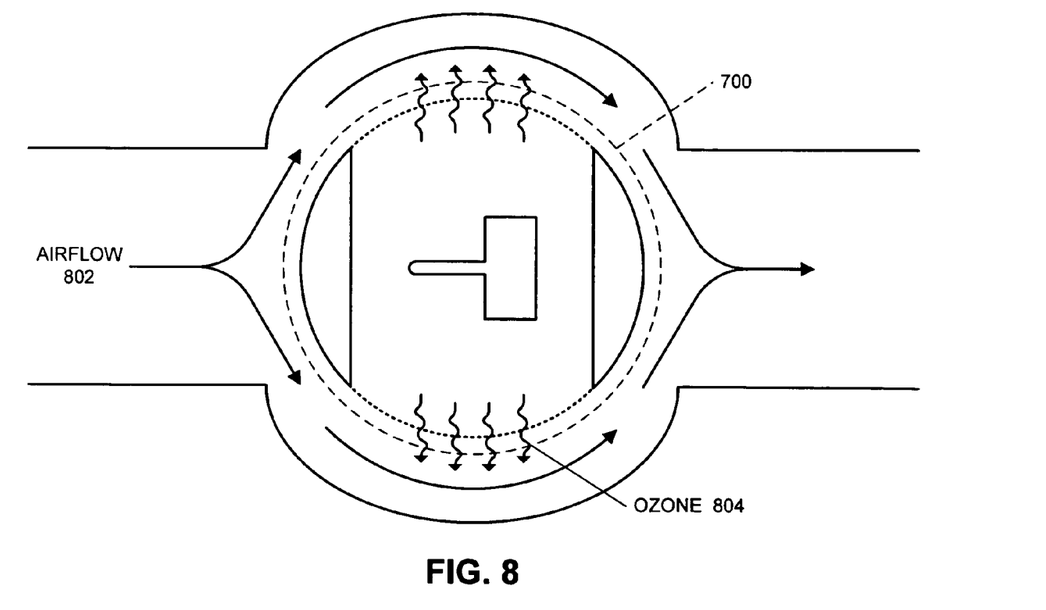
FIG. 8 illustrates the process of diffusing ozone into an air flow in accordance with an embodiment of the present invention.

FIG. 8 illustrates diffusing ozone into an air flow in accordance with an embodiment of the present invention. As illustrated in FIG. 8, ozone generator 700 is embedded in a pipe or tubing which directs airflow 802 past ozone generator 700. Ozone 804 diffuses out of ozone generator 700 into airflow 802. Ozone 802 can kill pathogens such as bacteria and viruses within airflow 802.

Alternate Ozone Diffusing Unit

Figure 9:
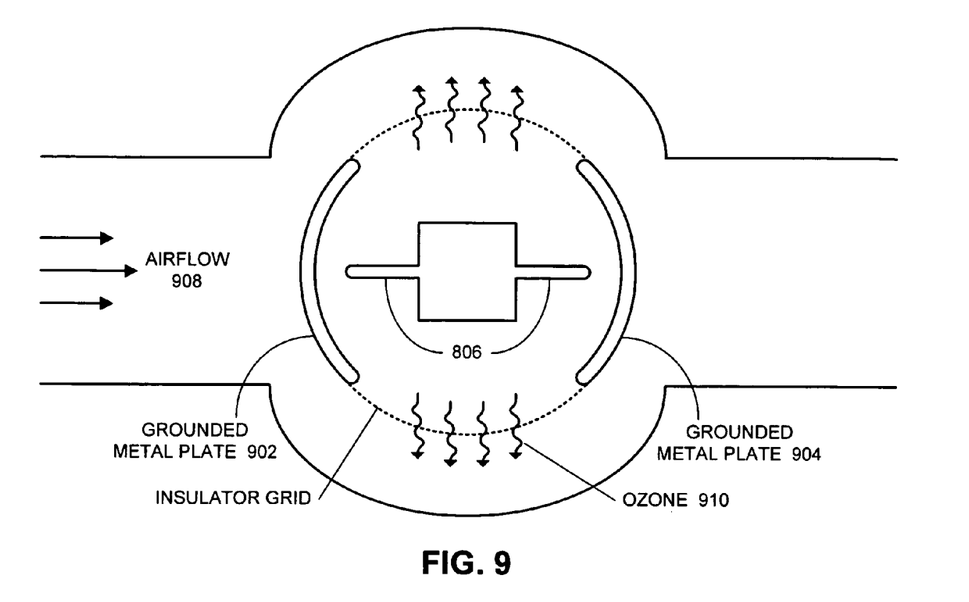
FIG. 9 illustrates an alternate method of diffusing ozone into an air flow in accordance with an embodiment of the present invention.

FIG. 9 illustrates an alternate method of diffusing ozone into an air flow in accordance with an embodiment of the present invention. In the configuration illustrated in FIG. 9, the ozone generator includes two high-voltage tips 902, one high voltage tip facing grounded metal plate 902 and one high voltage tip facing grounded metal plate 904. Ozone 910 diffuses into airflow 908 in the same manner described above in conjunction with FIG. 8.

Purifying Water

Figure 10:
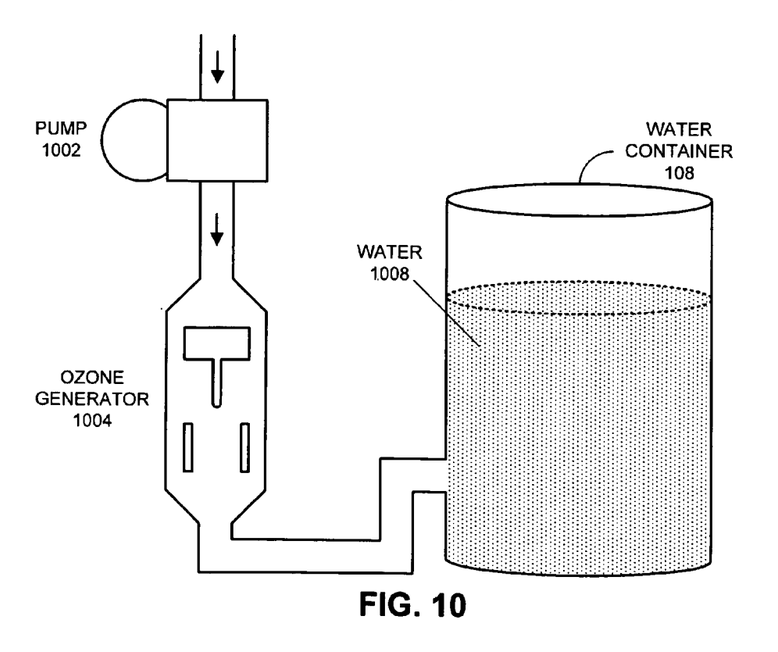
FIG. 10 illustrates purifying water in accordance with an embodiment of the present invention.

FIG. 10 illustrates purifying water in accordance with an embodiment of the present invention. Pump 1002 pumps air through ozone generator 1004 and into water container 1006. The air with the infused ozone bubbles through water 1008 in water container 1006 killing nano-organisms, such as bacteria and viruses.

The foregoing descriptions of embodiments of the present invention have been presented for purposes of illustration and description only. They are not intended to be exhaustive or to limit the present invention to the forms disclosed. Accordingly, many modifications and variations will be apparent to practitioners skilled in the art. Additionally, the above disclosure is not intended to limit the present invention. The scope of the present invention is defined by the appended claims.

What is claimed is:

1. An apparatus for ionizing gases and airborne particulates, comprising:
    at least one geometrically asymmetric electrode pair in any orientation, wherein electrodes in the electrode pair are spatially separated at no more than three millimeters;
    wherein the electrodes are comprised of an at least one type of electrically conductive material, wherein the at least one type of electrically conductive material includes, but is not limited to, metal, silicon, graphite, electrically conductive liquid, and electrically conductive gas;
    at least one type of electrically insulating material separating the electrodes, wherein the electrically insulating material includes, but is not limited to, glass, ceramic, plastic, oil, and gas; and
    at least one gaseous medium encapsulating the electrodes, wherein the gaseous medium includes, but is not limited to, nitrogen and oxygen;
    wherein the plurality of electrodes, the electrically insulating material, and the encapsulating gaseous medium form a miniature corona discharge based ionizer.

2. The apparatus of claim 1;
    wherein at least one of the electrodes is electrically stressed to any polarity;
    wherein at least one asymmetrical electrical field at a specified field strength is generated by the electrodes as a result of being electrically stressed;
    wherein the at least one asymmetrical electrical field is continuous or intermittent;
    wherein an electrical plasma, is generated near the surface of at least one electrode as a result of the asymmetrical electrical field, wherein the electrical plasma is continuous or intermittant; and
    wherein the electrical plasma generated is confined to the proximity of the surface of the electrode that has the higher electrical field density.

3. The apparatus of claim 1;
    wherein as a result of the generated plasma, a gaseous cloud of electrons, negative ions and positive ions are produced outside the plasma region; and
    wherein the gaseous cloud of electrons, negative ions, and positive ions charge separately and/or simultaneously liquid and/or solid phase airborne particulates, and ionize gases to produce charged gas molecules such as ozone.

4. The apparatus of claim 1;
    wherein the electrically insulating material includes, but is not limited to, an insulating substrate;
    wherein selected portions of the electrodes that perform mechanical and/or electrical contact with the substrate form the anchor;
    wherein the geometrically asymmetric electrodes includes, but is not limited to, electroplated structures that include at least one anchor;
    wherein the electroplated structures are attached onto the insulating substrate via the anchors;
    wherein the electroplated structures need not be confined to the same insulating substrate; and
    wherein the electroplated structures are encapsulated by air at standard atmospheric pressure and temperature, wherein the air includes any amount of humidity.

5. The apparatus of claim 4;
    wherein a protrusion structure on the at least one anchor that is separate from the insulating substrate forms the discharge tip;
    wherein the second electroplated structure forms one of, a grid and plate;
    wherein the second electroplated structure is of any geometry and orientation, including planar, cylindrical, semi-circular, ellipsoidal or curved;
    wherein the second electroplated structure forms the ground plane; and
        wherein the ground plane is used as a collection grid for airborne particulates.

6. The apparatus of claim 1;
    wherein the second electroplated structure is comprised of a paired structure, including, a parallel structure;
    wherein the protrusion structure is positioned between the paired structures; and
    wherein an air flow is passed between the protrusion structure and the paired structures at an angle, wherein the angle includes perpendicular to the electric field.

7. The apparatus of claim 1, further comprising differential mobility separator plates, wherein the differential mobility separator plates are configured to allow selected particulates to be passed to any form of particulate counting or detection mechanisms including a Faraday's cup and/or an optical detection unit for counting.

8. The apparatus of claim 1, further comprising differential mobility separator plates, which are configured to collect selected particles for counting.

9. The apparatus of claim 1, further comprising segmented differential mobility separator plates, wherein each segment of the segmented differential mobility separator plates collects a different electrical mobility particulate for counting.

10. The apparatus of claim 1, further comprising differential mobility separator plates, which are configured to separate particulate matter from an airflow, whereby the apparatus forms a filter mechanism.

11. The apparatus of claim 1;
wherein the protrusion structure is isolated from a main air flow through the apparatus; and
wherein the apparatus provides ozone to the main airflow.

12. The apparatus of claim 11;
wherein the apparatus is configured so that main airflow including ozone is passed through liquids including water and combinations thereof via mechanism including diffusion, aeration, and combinations thereof;
wherein the ozone kills and/or incapacitates allergens including spores, and/or pathogens including bacteria and viruses in the liquids; and
wherein the ozone kills and/or incapacitates allergens including spores, and/or pathogens including bacteria and viruses in gases including nitrogen, oxygen, carbon dioxide, and combinations thereof.

13. A means for ionizing gases and airborne particulates, comprising:
at least one geometrically asymmetric electrode pair means in any orientation, wherein the electrodes means are spatially separated at no more than three millimeters;
wherein the at least one geometrically asymmetric electrode pair means are comprised of at least one type of electrically conductive material including, but not limited to, metal, silicon, graphite, electrically conductive liquid, and electrically conductive gases;
at least one type of electrically insulating material means separating the electrodes means, wherein the at least one type of electrically insulating material means includes, but not limited to, glass, ceramic, plastic, oil, and gas; and
at least one type of gaseous medium means encapsulating the electrodes means, wherein the gaseous medium means includes, but is not limited to, nitrogen and oxygen;
wherein the plurality of electrodes means, the electrically insulating materials means and the encapsulating gaseous medium means form a miniature corona discharge based ionizer means.

14. The means of claim 13;
wherein at least one of the electrodes means is electrically stressed to any polarity;
wherein at least one asymmetrical electrical field means is generated by the electrodes means as a result of being electrically stressed;
wherein one electrical plasma means, is generated near the surface of at least one electrode means as a result of the asymmetrical electrical field means at a sufficient field strength, wherein the electrical plasma means is continuous and/or intermittent; and
wherein the electrical plasma means generated is typically confined to the proximity of the surface of the electrode means that has the higher electrical field density.

15. The means of claim 13;
wherein as the result of the plasma means generated, a gaseous cloud of electrons, negative ions, and positive ions is produced; and
wherein the gaseous cloud of electrons, negative and positive ions is used for charging both liquid and solid phase airborne particulates, and for ionization of gases to produce charged gas molecules such as ozone.

16. The apparatus of claim 13;
wherein the electrically insulating material means includes, but is not limited to, an insulating substrate;
wherein the geometrically asymmetric electrodes means includes, but is not limited to, electroplated structures that include anchors means;
wherein selected portions of the electrodes means that perform mechanical and/or electrical contact with the substrate form the anchor means;
wherein the electroplated structures are attached onto the insulating substrate via the anchors means;
wherein the electroplated structures means need not be confined to the same insulating substrate; and
wherein the electroplated structures means are encapsulated by, but not limited to, air at standard atmospheric pressure and temperature, wherein the air includes any amount of humidity.

17. The means of claim 16;
wherein a protrusion structure means on the anchor means that is separate from the insulating substrate means forms a discharge tip;
wherein the second electroplated structure means includes one of a grid and plate of any geometry and orientation, wherein the second electroplated structure is one of planar, cylindrical, semi-circular, ellipsoidal, and curved, and wherein the second electroplated structure forms a ground plane; and
wherein the ground plane can be used as a collection grid for airborne particulates.

18. The means of claim 13;
wherein the second electroplated structure means is comprised of a paired structure including, but not limited to, a parallel structure;
wherein the protrusion structure means is positioned between the paired structures; and
wherein an airflow is passed between the protrusion structure means and the paired structures at an angle, wherein the angle includes perpendicular to the electric field.

19. The means of claim 13, further comprising differential mobility separator plates means, wherein the differential mobility separator plats means is configured to allow selected particulates to be passed to an particulate counting and/or detection mechanisms including a Faraday's cup and/or an optical detection unit for counting.

20. The means of claim 13, further comprising differential mobility separator plates means, wherein the differential mobility separator plates means are configured to collect selected particles for counting.

21. The means of claim 13, further comprising segmented differential mobility separator plates means, wherein each segment of the segmented differential mobility separator plates means collects a different electrical mobility particulate for counting.

22. The means of claim 13, further comprising differential mobility separator plates means, wherein the differential mobility separator plates means are configured to separate particulate matter from an air flow, whereby the apparatus forms a filter mechanism.

23. The means of claim 13;
wherein the ionizing means is isolated from a main air flow through the apparatus; and
wherein the ionizing means provides ozone to the main air flow.

24. The means of claim 23;
wherein the ionizing means is configured so that main gas including airflow with ozone is passed through liquids including water and combinations thereof via mechanisms including diffusion, aeration, and combinations thereof;

wherein the ozone kills and/or incapacitates allergens including spores and/or pathogens including bacteria and viruses in the liquids;

wherein the apparatus is configured so that ozone is passed into the main gas flow including nitrogen, carbon dioxide, and combinations thereof; and wherein the ozone kills and/or incapacitates allergens including spores and/or pathogens including bacteria and viruses in the gas.

25. A system for ionizing airborne particulates, comprising:

a microfabricated miniature corona discharge ionizer, wherein the microfabricated miniature corona discharge ionizer ionizes particulates;

at least one power supply coupled to the microfabricated miniature corona discharge ionizer; and a microfabricated airborne particulate selection element positioned proximate to the microfabricated miniature corona discharge ionizer;

wherein the microfabricated airborne particulate selection element selects particulates based on particulate electrical mobility.

26. The system of claim 25, wherein the microfabricated airborne particulate selection element removes substantially all of the particulates from an air stream;

whereby the system functions as an air andlor gas filter.

* * * * *